United States Patent
Hoesel et al.

(10) Patent No.: US 7,482,145 B2
(45) Date of Patent: Jan. 27, 2009

(54) DEGLYCOSYLATED ENZYMES FOR CONJUGATES

(75) Inventors: Wolfgang Hoesel, Tutzing (DE); Werner Hoelke, Penzberg (DE); Beata Kanne, Neuried (DE); Helmut Lenz, Tutzing (DE); Rainer Mueller, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/227,881

(22) Filed: Sep. 15, 2005

(65) Prior Publication Data

US 2006/0040345 A1 Feb. 23, 2006

Related U.S. Application Data

(63) Continuation of application No. PCT/EP2004/002707, filed on Mar. 17, 2004.

(30) Foreign Application Priority Data

Mar. 17, 2003 (EP) ................... 03005930

(51) Int. Cl.
*C12N 9/96* (2006.01)
*C12N 9/12* (2006.01)
(52) U.S. Cl. ............... 435/188; 435/194; 424/9.34
(58) Field of Classification Search ............ 435/194, 435/975, 188; 536/23.2; 424/193.1, 9.34, 424/7.92
See application file for complete search history.

(56) References Cited

U.S. PATENT DOCUMENTS

| | | | |
|---|---|---|---|
| 4,275,149 A | 6/1981 | Litman et al. | |
| 4,683,293 A | 7/1987 | Craig | |
| 4,808,537 A | 2/1989 | Stroman et al. | |
| 4,812,405 A | 3/1989 | Lair et al. | |
| 4,818,700 A | 4/1989 | Cregg et al. | |
| 4,837,148 A | 6/1989 | Cregg | |
| 4,855,231 A | 8/1989 | Stroman et al. | |
| 4,857,467 A | 8/1989 | Sreekrishna et al. | |
| 4,879,231 A | 11/1989 | Stroman et al. | |
| 4,882,279 A | 11/1989 | Cregg | |
| 4,885,242 A | 12/1989 | Cregg | |
| 4,895,800 A | 1/1990 | Tschopp et al. | |
| 4,929,555 A | 5/1990 | Cregg et al. | |
| 5,002,876 A | 3/1991 | Sreekrishna et al. | |
| 5,004,688 A | 4/1991 | Craig et al. | |
| 5,032,516 A | 7/1991 | Cregg | |
| 5,122,465 A | 6/1992 | Cregg et al. | |
| 5,135,868 A | 8/1992 | Cregg | |
| 5,166,329 A | 11/1992 | Cregg | |
| 5,185,243 A | 2/1993 | Ullman et al. | |
| 5,618,676 A | 4/1997 | Hitzeman et al. | |
| 5,854,018 A | 12/1998 | Hitzeman et al. | |
| 5,856,123 A | 1/1999 | Hitzeman et al. | |
| 5,866,322 A * | 2/1999 | Jou et al. ............... 435/5 |
| 5,919,651 A | 7/1999 | Hitzeman et al. | |

FOREIGN PATENT DOCUMENTS

| | | |
|---|---|---|
| EP | 0955369 A2 | 11/1999 |
| EP | 1176205 A2 | 1/2002 |
| WO | WO 95/04069 | 2/1995 |
| WO | WO 96/15244 | 5/1996 |
| WO | WO 00/56903 | 9/2000 |
| WO | WO 2004/083862 A1 | 9/2004 |

OTHER PUBLICATIONS

Manes et al. JBC 273(36): 23353-60, 1998.*
Sigma (1993) catalog Nos. A7554, B9780, F0273 or B0774.*
McComb, R. et al., "Alkaline Phosphatase," Plenum Press, New York, 1979.
"Recommendations of the German Society for Clinical Chemistry; Standardization of methods for determining enzyme activities in biological fluids," Z. Klin. Chem. U. klin.Biochem., 10(1972) 182-192.
"Recommendations of the German Society for Clinical Chemistry; Standardisation of methods for the estimation of enzyme activity in biological fluids," Z. Klin. Chem.U. Klin. Biochem. 8(1970) 658-660.
Barbaric, S. et al., Database-Arch. Biorchem Biophys. 234(1984) p. 567-575, XP-002251233.
Bayer, E. et al., "Enzyme-Based Detection of Glycoproteins on Blot Transfers Using Avidin-Biotin Technology," Analytical Biochemistry 161, 123-131 (1987).
Besman, M. et al., "Isozymes of Bovine Intestinal Alkaline Phosphatase," The Journal of Biological Chemistry, vol. 260, No. 20, Sep. 15, 1985, p. 11190-11193.
Bretthauer, R. et al., "Glycosylation of *Pichia pastoris*-derived proteins," Biotechnol. Appl. Biochem. (1999) 30, 193-200.

(Continued)

*Primary Examiner*—Tekchand Saidha
(74) *Attorney, Agent, or Firm*—Marilyn Amick; Roche Diagnostics Operations, Inc.

(57) ABSTRACT

By deglycosylating an enzyme derived from a eukaryotic organism prior to forming a conjugate, i.e. prior to attaching the enzyme to a molecule capable of binding to a target molecule, the sensitivity of an assay for detecting the presence or determining the quantity of a target molecule, in which the conjugate is used as a labelled component, can be increased. The present invention provides conjugates, methods for providing the same, use of such conjugates as well as kits containing the conjugates.

12 Claims, 5 Drawing Sheets

OTHER PUBLICATIONS

Chu, F. et al., "Requirements of Cleavage of High Mannose Oligosaccharides in Glycoproteins by Peptide N-Glycosidase F," The Journal of Biological Chemistry, vol. 261, No. 1, Jan. 5, 1986, p. 172-177.

Dell, A., "F.A.B.-Mass Spectrometry of Carbohydrates," Advances in Carbohydrate Chemistry and Biochemistry, vol. 45, (1987), p. 19-72.

Edge, A. et al., "Deglycosylation of Glycoproteins by Trifluoromethanesulfonic Acid," Analytical Biochemistry 118, 131-137 (1981).

Fellinger, A. et al., Database—Yeast 7 (1991) 643-673, XP002251234.

Geisow, M., "Shifting Gear in Carbohydrate Analysis," Bio/Technology vol. 10, Mar. 1992, p. 277-280.

Harris, H., "The human alkaline phosphatases: what we know and what we don't know," Clinica Chimica Acta, 186 (1989) 133-150.

Haselbeck, A. et al., "Studies on the effect of the incubation conditions, various detergents and protein concentration on the enzymatic activity of N-Glycosidase F (Glycopeptidase F) and Endoglycosidase F," Topics in Biochemistry, Boehringer Mannheim GmbH, No. 8 (1988), p. 1-4.

Heimo, E. et al., "Human Placental Alkaline Phosphatase: Expression in *Pichia pastoris*, Purification and Characterization of the Enzyme," Protein Expression and Purification 12, 85-92 (1986).

Hermanson, G., "Bioconjugate Techniques," Chapter 16, Academic Press, Inc., 1996, pp. 630-638.

Houba, P. et al., "Improved Characteristics of a Human β-Glucuronidase-Antibody Conjugate after Deglyosylation for Use in Antibody-Directed Enzyme Prodrug Therapy," Bioconjugate Chem. 1996, 7, 606-611.

Janknecht, R. et al., "Rapid and efficient purification of native histidine-tagged protein expressed by recombinant vaccinia virus," Proc. Natl. Acad. Sci. USA, vol. 88, Oct. 1991, p. 8972-8976.

Kobata, A. et al., "Use of Endo- and Exoglycosidases for Structural Studies of Glycoconjugates," Analytical Biochemistry 100, 1-14 (1979).

Lee, K. et al., "Carbohydrate Analysis of Glycoproteins, A Review," Applied Biochemistry and Biotechnology, vol. 23, p. 53-80 (1990).

Lundbald, R., Comment Glycosylation in *Pichia pastoris*, Biotechnol. App. Biochem. (1999) 30, 191-191.

Millán, J., "Oncodevelopmental Expression and Structure of Alkaline Phosphatase Genes," Anticancer Research 8: 995-1004 (1988).

Nosjean, O. et al., "Human tissue non-specific alkaline phosphatases: sugar-moeity-induced enzymic and antigenic modulations and genetic aspects," Boichem. J. (1997) 321, 297-303.

O'Sullican, M. et al., "Methods for the Preparation of Enzyme-Antibody Conjugates for Use in Enzyme Immunoassay," Methods in Enzymology, vol. 73, (1981) 147-166.

Sojar, H. et al., "A Chemical Method for the Deglycosylation of Proteins," vol. 259, No. 1, Nov. 15, 1987, p. 52-27.

Spellman, M. et al., "Carbohydrate Characterization of Recombinant Glycoproteins of Pharmaceutical Interest," Anal. Chem. 1990, 62, p. 1714-1722.

Tanner, W. et al., "Protein glycosylation in yeast," Biochimica et Biophysica Acta 906 (1987) 81-99.

Tarentino, A., "Deglycosylation of Asparagine-Linked Glycans by Peptide: N-Glycosidase F," Biochemistry 1985, 24, 4665-4671.

Thotakura, N. et al., "Enzymatic Deglycosylation of Glycoproteins," Methods in Enzymology, vol. 138 (1987) 350-359.

Trimble, R. et al., "Optimizing Hydrolysis of N-Linked High-Mannose Oligosaccharides by Enod-β-N-acetylglucosaminidase H," Analytical Biochemistry 141, 515-522 (1984).

Vliegenthart, J. et al., "High-resolution, H-Nuclear Magnetic Resonance Spectroscopy as a Tool in the Structural Analysis of Carbohydrates Related to Glycoproteins," Advances in Carbohydrate Chemistry and Biochemistry, vol. 41, p. 209-374, (1983).

* cited by examiner

A: conjugation mixture recAP / anti-hCG-IgG

B: conjugation mixture recAP (endo H treated) / anti-hCG-IgG

SEQUENCE LISTING

<160> NUMBER OF SEQ ID NOS: 1

<210> SEQ ID NO 1
<211> LENGTH: 487
<212> TYPE: PRT
<213> ORGANISM: Bos taurus
<220> FEATURE:
<221> NAME/KEY: MISC_FEATURE
<223> OTHER INFORMATION: bIAP II amino acid sequence

<400> SEQUENCE: 1

```
Leu Ile Pro Ala Glu Glu Asn Pro Ala Phe Trp Asn Arg Gln Ala
 1               5                  10                  15

Ala Gln Ala Leu Asp Val Ala Lys Lys Leu Gln Pro Ile Gln Thr Ala
            20                  25                  30

Ala Lys Asn Val Ile Leu Phe Leu Gly Asp Gly Met Gly Val Pro Thr
        35                  40                  45

Val Thr Ala Thr Arg Ile Leu Lys Gly Gln Met Asn Gly Lys Leu Gly
50                  55                  60

Pro Glu Thr Pro Leu Ala Met Asp Gln Phe Pro Tyr Val Ala Leu Ser
65                  70                  75                  80

Lys Thr Tyr Asn Val Asp Arg Gln Val Pro Asp Ser Ala Gly Thr Ala
                85                  90                  95

Thr Ala Tyr Leu Cys Gly Val Lys Gly Asn Tyr Arg Thr Ile Gly Val
            100                 105                 110

Ser Ala Ala Arg Tyr Asn Gln Cys Asn Thr Thr Arg Gly Asn Glu
        115                 120                 125

Val Thr Ser Val Ile Asn Arg Ala Lys Lys Ala Gly Lys Ala Val Gly
130                 135                 140

Val Val Thr Thr Thr Arg Val Gln His Ala Ser Pro Ala Gly Ala Tyr
145                 150                 155                 160

Ala His Thr Val Asn Arg Asn Trp Tyr Ser Asp Ala Asp Leu Pro Ala
                165                 170                 175

Asp Ala Gln Lys Asn Gly Cys Gln Asp Ile Ala Ala Gln Leu Val Tyr
            180                 185                 190

Asn Met Asp Ile Asp Val Ile Leu Gly Gly Gly Arg Met Tyr Met Phe
        195                 200                 205

Pro Glu Gly Thr Pro Asp Pro Glu Tyr Pro Asp Asp Ala Ser Val Asn
210                 215                 220

Gly Val Arg Lys Asp Lys Gln Asn Leu Val Gln Glu Trp Gln Ala Lys
225                 230                 235                 240

His Gln Gly Ala Gln Tyr Val Trp Asn Arg Thr Ala Leu Leu Gln Ala
                245                 250                 255

Ala Asp Asp Ser Ser Val Thr His Leu Met Gly Leu Phe Glu Pro Ala
            260                 265                 270

Asp Met Lys Tyr Asn Val Gln Gln Asp His Thr Lys Asp Pro Thr Leu
        275                 280                 285

Ala Glu Met Thr Glu Ala Ala Leu Gln Val Leu Ser Arg Asn Pro Arg
290                 295                 300

Gly Phe Tyr Leu Phe Val Glu Gly Gly Arg Ile Asp His Gly His His
305                 310                 315                 320

Asp Gly Lys Ala Tyr Met Ala Leu Thr Glu Ala Ile Met Phe Asp Asn
                325                 330                 335

Ala Ile Ala Lys Ala Asn Glu Leu Thr Ser Glu Leu Asp Thr Leu Ile
            340                 345                 350

Leu Val Thr Ala Asp His Ser His Val Phe Ser Phe Gly Gly Tyr Thr
        355                 360                 365

Leu Arg Gly Thr Ser Ile Phe Gly Leu Ala Pro Gly Lys Ala Leu Asp
370                 375                 380

Ser Lys Ser Tyr Thr Ser Ile Leu Tyr Gly Asn Gly Pro Gly Tyr Ala
385                 390                 395                 400
```

```
                          -continued

Leu Gly Gly Gly Ser Arg Pro Asp Val Asn Gly Ser Thr Ser Glu Glu
                405                 410             415

Pro Ser Tyr Arg Gln Gln Ala Ala Val Pro Leu Ala Ser Glu Thr His
            420                 425             430

Gly Gly Glu Asp Val Ala Val Phe Ala Arg Gly Pro Gln Ala His Leu
            435             440             445

Val His Gly Val Gln Glu Thr Phe Val Ala His Ile Met Ala Phe
        450             455             460

Ala Gly Cys Val Glu Pro Tyr Thr Asp Cys Asn Leu Pro Ala Pro Ala
465             470             475             480

Thr Ala Thr Ser Ile Pro Asp
                485
```

DEGLYCOSYLATED ENZYMES FOR CONJUGATES

RELATED APPLICATIONS

This application is a continuation of PCT application PCT/EP2004/002707 filed Mar. 17, 2004 and claims priority to European application EP 03005930.7 filed Mar. 17, 2003.

FIELD OF THE INVENTION

The present invention pertains to conjugates comprising an enzyme. More specifically, the present invention pertains to conjugates comprising a glycosylated enzyme, whereby the glycosylated enzyme has been produced by recombinant means in a eukaryotic microbial host.

BACKGROUND OF THE INVENTION

Glycoproteins are glycosylated polypeptides. Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of sugars, e.g., N-acetylgalactosamine, galactose, or xylose to a hydroxylamino acid, most commonly serine or threonine, although 5-hydroxyproline or 5-hydroxylysine may also be used. The N-linked oligosaccharides are further differentiated into 3 subgroups, these being the high mannose type, the complex type, and the hybrid type. N-linked oligosaccharides are frequently branched, where branching commonly occurs either at a mannose residue or at an N-acetylglucosamine residue. These branched structures are called biantennary, if there are two branches, and triantennary if there are three branches.

Existing methods for analyzing carbohydrate structure rely on complex multi-step procedures. These procedures involve techniques such as mass spectrometry, NMR, fast atom bombardment, complex chromatography techniques (high pressure liquid chromatography, gas phase chromatography, ion-exchange and reverse-phase chromatography) and complex series of chemical reactions (methylation analysis, periodate oxidation, and various hydrolysis reactions) and have all been used in various combinations to determine the sequence of oligosaccharides and the features of their glycosidic linkage. Each method can provide certain pieces of information about carbohydrate structure, but each has disadvantages. For example, fast atom bombardment (Dell, A., Adv. Carbohydr. Chem. Biochem. 45 (1987) 19-72) can provide some size and sequence data but does not provide information on linkage positions or anomeric configuration. NMR is the most powerful tool for analyzing carbohydrates (Vliegenthart et al., Adv. Carbohydr. Chem. 41 (1983) 209-375) but is relatively insensitive and requires large quantities of analyte. These methods have been reviewed by Spellman, M. W., Anal. Chem. 62 (1990) 1714-1722; Lee, K. B., et al., Appl. Biochem. Biotechnol. 23 (1990) 53-80; and Geisow, M. J., Bio/technology 10 (1992) 277-280.

Removal of carbohydrate moieties from a purified glycosylated protein may be accomplished chemically or enzymatically. For instance, chemical deglycosylation by exposing the polypeptide to the compound trifluoromethanesulfonic acid or an equivalent compound can result in the cleavage of most or all sugars except the linking sugar (N-acetylglucosamine or N-acetylgalactosamine), while leaving the polypeptide intact. Chemical deglycosylation is described by Sojar, H. T., and Bahl, O. P., Arch. Biochem. Biophys. 259 (1987) 52-57, and by Edge, A. S. B., et al., Anal. Biochem. 118 (1981) 131-137. Enzymatic cleavage of carbohydrate moieties on polypeptides can be achieved by the use of a variety of endo- and exo-glycosidases as described by Thotakura, N. R., and Bahl, O. P., Meth. Enzymol. 138 (1987) 350-359.

There are glycosylated enzymes known to the art where the carbohydrate moiety is required for maintaining enzymatic activity. An example therefor has been described by Barbaric, S., et al., Arch. Biochem. Biophys. 234 (1984) 567-575. Acid phosphatase, purified from the yeast *Saccharomyces cerevisiae*, was deglycosylated by endo-β-N-acetylglucosaminidase H or by HF treatment. The 90% deglycosylated enzyme showed a pronounced loss of enzyme activity, accompanied by the disruption of the three-dimensional structure.

Houba, H. J. et al. Bioconjugate Chem. 7 (1996) 606-611 describe the modification of human beta-glucuronidase using $NaIO_4$ and $NaBH_4$, to improve the retention of the enzyme in the circulation. The modified enzyme was used to prepare immunoconjugates.

Expression of heterologous proteins in yeast often results in heavily glycosylated proteins with a high mannose content (Tanner, W., and Lehle, L., Biochim Biophys Acta 906 (1987) 81-99). One example therefor is alpha-galactosidase from the plant *Cyamopsis tetragonoloba* (guar) which was produced as a heterologous protein in the methylotrophic yeast *Hansenula polymorpha* (Fellinger, A. J., et al., Yeast 7 (1991) 463-473). In *C. tetragonoloba* the alpha-galactosidase is a glycoprotein. The alpha-galactosidase secreted by *H. polymorpha* was also glycosylated and had a sugar content of 9.5%. The specific activity of the alpha-galactosidase produced by *H. polymorpha* was 38 U/mg compared to 100 U/mg for the native guar alpha-galactosidase. Notably, deglycosylation of the alpha-galactosidase restored the specific activity completely.

Purifying from native mammalian host tissue a protein to be used for forming a conjugate bears the risk that an unwanted compound such as an inhibitor or a pathogen may copurify. E.g., bovine alkaline phosphatase isolated from bovine tissue may be contaminated with pathogenic bovine prion protein. For this reason, recombinant expression of the desired protein in a microbial host such as yeast is preferred. Very much preferred is a methylotrophic yeast as a microbial host. Expression of a desired protein in yeast can take advantage of intracellular trafficking pathways such as the secretory pathway which includes modification of the desired protein by glycosylation.

EP 1,176,205 discloses highly active eukaryotic alkaline phosphatase expressed as a heterologous protein in *Pichia pastoris* which is also glycosylated by the yeast when targeted to the secretory pathway. Notably, the properties of the yeast-derived enzyme are similar to those of the native glycosylated enzyme purified from bovine intestine.

Accordingly, the specific activity of the alkaline phosphatase expressed as a heterologous protein in *Pichia pastoris* is reported to have a specific activity of 7,000 U/mg. Thus, the yeast-specific carbohydrate moiety does not interfere with the enzymatic activity of the free enzyme.

Alkaline phosphatase is an example of an enzyme that is used frequently as a label in analytical methods for the detection of chemical or biological substances. Most of these methods rely on what are known as "specific binding" reactions in which a substance to be detected, referred to as a "target molecule" or "analyte", reacts specifically and preferentially with a corresponding "molecule capable of binding to a target molecule" or "receptor". Most well-known specific binding reactions occur between immunoreactants, e.g., antibodies, and antigens or haptens. By "hapten" is meant any molecule which can act as an antigen but which is incapable by itself of eliciting an immune response. In order to elicit an appropriate antibody response, a hapten can be bound, typically via covalent attachment, to an immunogenic carrier to produce an immunogenic conjugate capable of eliciting antibodies specific for the hapten.

Also known are other specific binding reactions, such as avidin or streptavidin with biotin, a carbohydrate with a lectin, or a hormone with a hormone receptor. In addition, the term "specific binding" also includes the interaction of complementary nucleic acids or analogs thereof in a hybridization reaction. Moreover, the term "specific binding" is known to occur between a protein and a nucleic acid or a nucleic acid analog. An example of a nucleic acid analog is a phosphorothioate or a peptide nucleic acid ("PNA").

Since samples to be analyzed contain the target molecules often in very small amounts, methods based on immunoassays are preferably used for their detection with which the target molecules can be determined very specifically and exactly. There are many variants of these methods. The various immunological methods of determination may be classified into homogeneous and heterogeneous methods. A solid phase reaction always forms part of the "heterogeneous" method in order to immobilize complexes which contain the substance to be detected and a labelled component, and thus to separate them from unbound labelled components. In the "homogeneous" method variant there is no separation of bound label and unbound label so that bound and unbound label have to be differentiated by other methods.

The "label" is any molecule that produces or can be induced to produce a signal. There are many different "labelled components" known for immunoassays. One part of a labelled component, the label, is an enzyme that needs one or several additional components to produce a signal, and the signal producing system would then include all the components required to produce a measurable signal. Thus, the signal is detected and/or measured by detecting the activity of the enzyme. The additional components may include substrates, coenzymes, enhancers, additional enzymes, substances that react with products that are generated by enzymatic activity, catalysts, activators, cofactors, inhibitors, scavengers, metal ions, and a specific binding substance required for binding of signal generating substances. A detailed discussion of suitable signal producing systems can be found in U.S. Pat. No. 4,275,149 and U.S. Pat. No. 5,185, 243. Examples of enzymes and substrates include, for example: (a) horseradish peroxidase with hydrogen peroxide as a substrate, wherein the hydrogen peroxide oxidizes a dye precursor, e.g., orthophenylene diamine or 3,3',5,5'-tetramethyl benzidine hydrochloride; (b) alkaline phosphatase with para-nitrophenyl phosphate as chromogenic substrate; and (c) β-D-galactosidase with a chromogenic substrate, e.g., o-nitrophenyl-β-D-galactopyranoside or with a fluorogenic substrate 4-methylumbelliferyl-β-D-galactopyranoside. However, numerous other enzyme-substrate combinations are known to a person skilled in the art.

Another part of a labelled component is a molecule capable of binding to a target molecule, exemplified by an antibody or a functional fragment of an antibody. Single chain antibodies and chimeric, humanized or primatized (CDR-grafted) antibodies, as well as chimeric or CDR-grafted single chain antibodies, and the like, comprising portions derived from different species, are also encompassed by the term "antibody" as used herein. The various portions of these antibodies can be joined together chemically by conventional techniques, or can be prepared as a contiguous protein using genetic engineering techniques. In addition, functional fragments of antibodies, including fragments of chimeric, humanized, primatized or single chain antibodies, can also be produced. Functional fragments of the foregoing antibodies retain at least one binding function of the full-length antibody from which they are derived. Preferred functional fragments retain an antigen-binding function of a corresponding full-length antibody. Other examples of a molecule capable of binding to a target molecule in a labelled component are avidin, streptavidin, lectins, nucleic acids or analogs thereof.

A labelled component that comprises two portions, that is to say an enzyme and a molecule capable of binding to a target molecule, can be obtained by forming a "conjugate", i.e. by conjugating the two portions. A conjugate is a molecule comprised of two or more molecules attached to one another, optionally through a linking group, to form a single structure. The binding can be made either by a direct connection between the molecules or by means of a linking group. An overview on the formation of conjugates, particularly the conjugation of enzymes can be found in Hermanson, G. T., In: Bioconjugate Techniques, Ch. 16, Academic Press, 1996, pp. 630-638. Techniques for conjugating enzymes to proteins are described in O'Sullivan, M. J., and Marks, V., Methods Enzymol. 73 (1981) 147-166.

In a conjugate, the function, that is to say, the activity of the enzyme which is comprised therein as a label can be impaired due to several reasons. For example, in the conjugate the enzyme may have an altered and suboptimal conformation. Another example is an interaction of the enzyme with a molecule with which it forms the conjugate, e.g. an antibody. In such a case impaired enzyme activity in the conjugate could result from steric effects that reduce, e.g., the access of a substrate to the catalytic center of the enzyme. Consequently, an assay for detecting the presence or determining the quantity of a target molecule such as an immunoassay (a detection assay) has a reduced sensitivity in case the labelled component is a conjugate comprising an enzyme with an impaired activity. Conversely, the sensitivity of a detection assay such as an immunoassay can be increased by removing any obstacles that impair the activity of the enzyme in the conjugate that is used in the assay as the labelled component.

SUMMARY OF THE INVENTION

It is against the above background that the present invention provides certain unobvious advantages and advancements over the prior art. In particular, the inventor has recognized a need for improvements in deglycosylated enzymes for conjugates.

It is therefore an object of the invention to provide an enzyme for preparing a conjugate as a labelled component that increases the sensitivity of an assay for detecting the presence or determining the quantity of a target molecule, whereby the enzyme is derived from a eukaryotic organism, i.e., has been expressed in and/or purified from a eukaryotic organism. It is a further object of the invention to provide an enzyme for preparing a conjugate as a labelled component that increases the sensitivity of an immunoassay, whereby the enzyme has been produced recombinantly in yeast, more particularly in methylotrophic yeast.

The inventors have surprisingly found that if an enzyme derived from a eukaryotic organism is deglycosylated prior to forming the conjugate, i.e., prior to attaching the enzyme to a molecule capable of binding to a target molecule, the sensitivity of the assay for detecting the presence or determining the quantity of a target molecule, in which the conjugate is used as a labelled component, is increased. Therefore, a first embodiment of the invention is a method to produce a conjugate of a molecule capable of binding to a target molecule and an enzyme, comprising the steps of (a) providing a glycosylated enzyme, (b) deglycosylating the enzyme of step (a), (c) isolating the deglycosylated enzyme, and (d) attaching the deglycosylated enzyme of step (c) to the molecule capable of binding to a target molecule. Another embodiment of the invention is a conjugate of a molecule capable of binding to a target molecule and an enzyme, obtainable by the method of the invention. Another embodiment of the invention is the use of a conjugate according to the invention in an assay for detecting the presence or determining the quantity of a target molecule. Yet another embodiment of the invention is a kit of parts, comprising a molecule capable of binding to a target molecule attached to a solid phase, a conjugate according to the invention, an incubation buffer, and a substrate capable of being converted by the enzyme portion of the conjugate.

BRIEF DESCRIPTION OF THE DRAWINGS

The following detailed description of the embodiments of the present invention can be best understood when read in conjunction with the following drawings, where like structure is indicated with like reference numerals and in which.

DETAILED DESCRIPTION OF THE INVENTION

Figure 1:
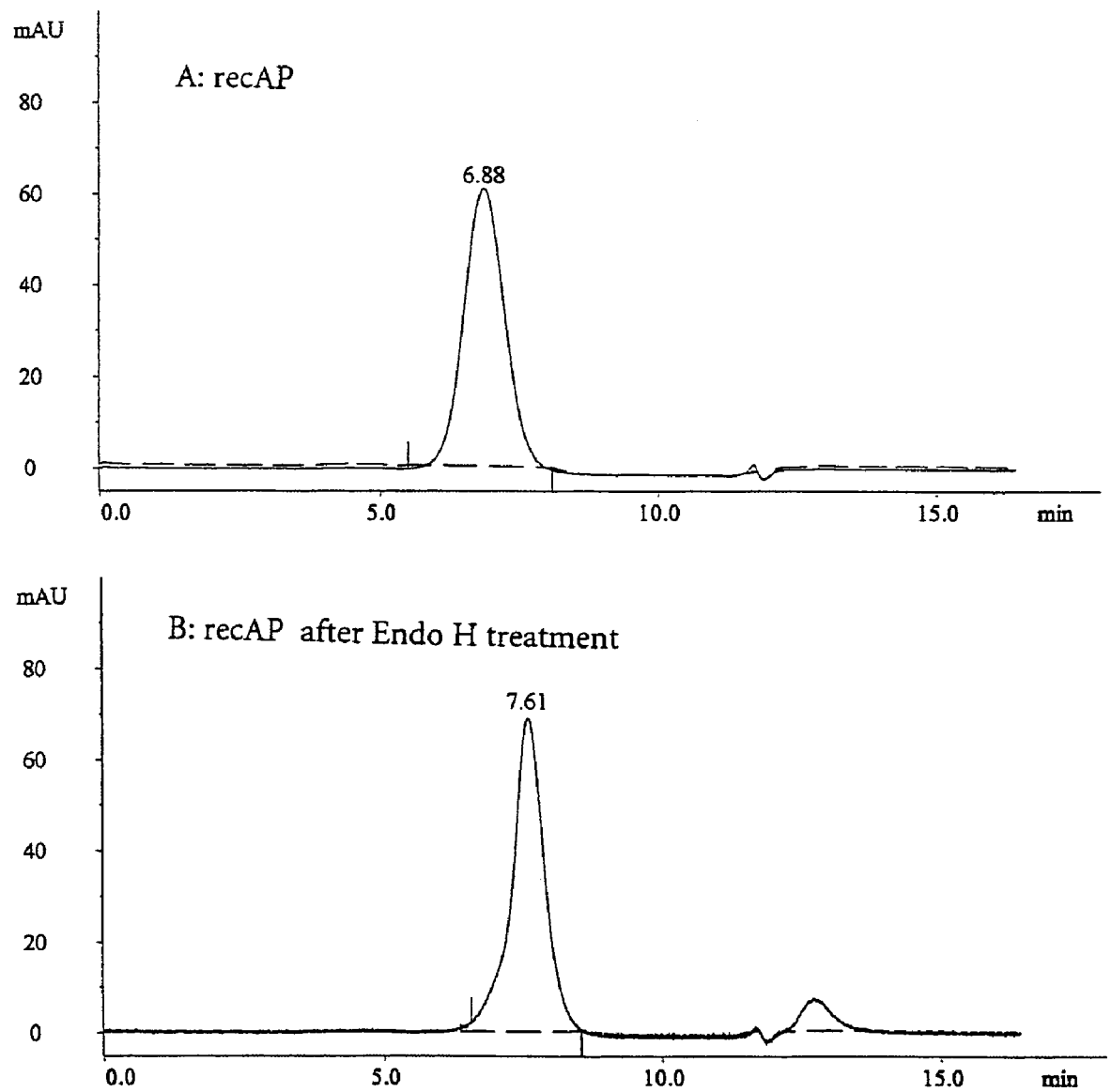
FIG. 1 is a graph showing elution on a TSK 3000 column of the recombinantly produced alkaline phosphatase (recAP) before (A) and after (B) an endo H treatment. The solid line demonstrates the protein absorption at 280 nm.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

There are numerous applications in the life sciences in which conjugates have a function. Conjugates result from the coupling of proteins such as enzymes to other molecules, such as a second protein, or a different class of molecule. An example of a second protein is an antibody or streptavidin. Biotin is an example of a molecule of a different class. Technologies of substantial importance in fields such as clinical diagnostics, immunology, and in vivo imaging rely on the use of these coupled protein reagents. Well known to the art are, e.g., conjugates comprising an antibody and an enzyme for use in an ELISA-type immunoassay. When considering forming a conjugate of a protein with another molecule, several approaches can be taken with regard to functional chemistry. A wider overview of applications of conjugates as well as of the different chemical ways to couple proteins with other molecules is given by Aslam M. and Dent A. (1998) Bioconjugation, Grove's Dictionaries, Inc., New York, particularly on pages 50-101.

On the one hand, the side chain functions of protein-forming amino acids can be used for coupling reactions when making conjugates. For instance, an ε-amino group of a lysine is highly reactive and the —$(CH_2)_4$— chain acts as a convenient spacer to distance the reaction site from the protein molecule. Derivatization of terminal amine groups can be achieved by way of reacting the amine group with aryl, sulfonyl or triazine halides, active carboxyl derivatives, aldehydes, iso(thio)cyanates, imidates, oxiranes, or haloacetyl derivatives. As another example, derivatization of protein thiol groups using oxiranes, maleimides, disulfides, haloacetyl compounds, mercurials, vinyl sulfones, aryl halides, as well as aziridines are well known to the art. The skilled artisan is also aware of numerous other derivatization methods of protein-forming amino acids such as those with carboxylate, carboxamide, and hydroxyl functions, and also tyrosine, tryptophane arginine, and methionine residues.

Glycoproteins, on the other hand, additionally offer carbohydrate residues for use in coupling reactions. As used herein, the term "carbohydrate residue" denotes a monomeric sugar subunit in a glycan. Carbohydrate residues can be derivatized, e.g., using epoxides, benzoquinone, or cyanogen bromide. Moreover, widespread use is made of periodate oxidation. Periodate is a powerful oxidizing agent and undergoes a reasonably specific reaction with sugar molecules containing hydroxyl groups on adjacent carbon atoms (vicinal diol), cleaving the carbohydrate ring and generating two aldehyde groups in each case. Aldehydes undergo a dehydration reaction with amines to yield an imine, so this is a means of coupling an amine-containing molecule to a sugar chain. For greater stability this bond is generally reduced to a substituted amine bond. Milder oxidizing reagents are also known to the skilled artisan and include enzymatic examples such as galactose oxidase. An alternative to aminolysis of the oxidized material is to react the aldehyde with hydrazides.

Expression of an enzyme which in its native form is glycosylated as a heterologous enzyme in yeast often results in a heavily glycosylated product. That is to say that more sugar residues are attached to the enzyme produced in yeast compared to the native form of the enzyme. In addition, the glycosylation pattern may be different compared to the native form of the enzyme.

Considering these differences of a glycosylated enzyme recombinantly expressed in yeast, under certain conditions the carbohydrate portion of the recombinantly expressed enzyme may have a negative impact on its performance when chemically linked to another protein to form a conjugate. Therefore, a first aspect of the invention is a method to produce a conjugate of a molecule capable of binding to a target molecule and an enzyme, comprising the steps of (a) providing a glycosylated enzyme, (b) deglycosylating the enzyme of step (a), (c) isolating the deglycosylated enzyme, and (d) attaching the deglycosylated enzyme of step (c) to the molecule capable of binding to a target molecule.

It is preferred that the enzyme of step (a) is obtained by expression in a transformed yeast and isolated therefrom. It is more preferred that the carbohydrate portion of the glycosylated enzyme contains multiple mannose subunits.

In a preferred embodiment of the invention, the amino acid sequence of the enzyme contains a glycosylation site. In another preferred embodiment of the invention, the enzyme is of eukaryotic origin. In yet another preferred embodiment, the enzyme is obtained by expressing in a eukaryotic host organism a genetic construct which codes for the enzyme. The term "expressing" includes post-translational modification and particularly glycosylation of the enzyme. In yet another preferred embodiment, the enzyme is of eukaryotic or procaryotic origin and obtained by expressing in a eukaryotic host organism a genetic construct which codes for the enzyme. In yet another preferred embodiment, the eukaryotic host organism is a yeast strain. Expression of a desired enzyme in yeast can take advantage of intracellular trafficking pathways such as the secretory pathway which includes modification of the desired enzyme by glycosylation. Expression of proteins in yeast is described in U.S. Pat. No. 5,618,676, U.S. Pat. No. 5,854,018, U.S. Pat. No. 5,856,123, and U.S. Pat. No. 5,919,651. In yet another preferred embodiment, the eukaryotic host organism is a methylotrophic yeast strain. In yet another preferred embodiment, the eukaryotic host organism is a methylotrophic yeast strain of the genus selected from the group consisting of *Pichia, Hansenula, Candida* and *Torulopsis*. In yet another preferred embodiment, the eukaryotic host organism is a methylotrophic yeast strain of the species *Pichia pastoris*. Well-established methods for expression of proteins in the methylotrophic yeast *Pichia pastoris* are described in U.S. Pat. No. 4,683,293, U.S. Pat. No. 4,808,537, U.S. Pat. No. 4,812,405, U.S. Pat. No. 4,818,700, U.S. Pat. No. 4,837,148, U.S. Pat. No. 4,855,231, U.S. Pat. No. 4,857,467, U.S. Pat. No. 4,879,231, U.S. Pat. No. 4,882,279, U.S. Pat. No. 4,885,242, U.S. Pat. No. 4,895,800, U.S. Pat. No. 4,929,555, U.S. Pat. No. 5,002,876, U.S. Pat. No. 5,004,688, U.S. Pat. No. 5,032,516, U.S. Pat. No. 5,122,465, U.S. Pat. No. 5,135,868, U.S. Pat. No. 5,166,329, and WO 00/56903. Isolation of desired protein from the host organism encompasses isolation from the host organism's biomass as well as from the medium in which the host organism is cultured.

Expression of heterologous proteins in yeast often results in heavily glycosylated proteins with a high mannose content (Tanner, W., and Lehle, L., Biochim Biophys Acta 906 (1987) 81-99). Thus, a heavily glycosylated protein comprises a carbohydrate portion containing multiple mannose subunits.

There are several methods known how to deglycosylate a glycoprotein, chemical methods and enzymatic methods. Chemical deglycosylation procedures using trifluoromethanesulfonic acid (TFMS) are well known to the person skilled in the art, as well as methods based on methanolysis or hydrofluoric acid (Edge, A. S. B., et al., Anal. Biochem. 118 (1981) 131-137; Sojar, H. T., and Bahl, O. P., Arch. Biochem. Biophys. 259 (1987) 52-57).

Peptide N-glycosidase F, also known as N-Glycosidase F (EC 3.2.218; 3.5.1.52) cleaves all types of asparagine-bound N-glycans, provided that the amino-group as well as the carboxyl group are present in a peptide linkage and that the oligosaccharide has the minimum length of the chitobiose core unit (Tarentino, A. L., et al., Biochemistry 24 (1985) 4665-4671; Chu, F. K., J. Biol. Chem. 261 (1986) 172-177). The reaction products are ammonia, aspartic acid (in the peptide chain) and the complete oligosaccharide. The reaction mechanism differs from that of endoglycosidases D, H and F. These enzymes cleave the glycosidic linkage between the two N-acetyl-glucosamine residues. They also show a more limited substrate specificity than N-glycosidase F. (Haselbeck, A., and Hoesel, W., Topics in Biochemistry (1988), Nr. 8, Boehringer Mannheim GmbH). Thus, N-Glycosidase F is not a glycosidase but an amidase as it converts asparagine to aspartic acid.

Enzymatic cleavage of carbohydrate moieties on polypeptides can be achieved using a variety of endo- and exo-glycosidases. Endo-β-N-acetylglucosaminidase H, also known as endoglycosidase H or endo H (EC 3.2.1.96) preferentially hydrolyzes N-glycans of the high mannose type (Kobata, A., Anal. Biochem. 100 (1979) 1-14; Trimble, R. B., and Maley, F., Anal. Biochem. 141 (1984) 515-522). Endoglycosidase H cleaves between the two N-acetylglucosamine residues in the diacetylchitobiose core of the oligo-saccharide, generating a truncated sugar molecule with one N-acetylglucosamine residue remaining on the asparagine. In contrast, Peptide N-glycosidase F removes the oligo-saccharide intact. Endo-β-N-acetylglucosaminidase F, also known as endoglycosidase F or endo F, cleaves within the diacetylchitobiose core of N-linked oligosaccharides leaving an N-acetyl-glucosamine residue attached to the asparagine. Endoglycosidase F preferentially acts on high-mannose-type N-glycanes.

Therefore, in yet another preferred embodiment of the invention, in step (b) of the method of the invention the enzyme is deglycosylated or partially deglycosylated by a chemical reagent, an amidase, an exoglycosidase, or an endoglycosidase. A preferred chemical reagent is anhydrous trifluoromethanesulfonic acid. In yet another preferred embodiment of the invention, in step (b) of the method of the invention the enzyme is deglycosylated or partially deglycosylated by endo-β-N-acetylglucosaminidase H, endo-β-N-acetylglucosaminidase F, or peptide-N-glycosidase F, or a combination thereof. Thus, the enzyme is deglycosylated by an enzyme selected from the group consisting of endo-β-N-acetylglucosaminidase H, endo-β-N-acetylglucosaminidase F, and peptide-N-glycosidase F, or by a combination thereof.

Example 1 describes deglycosylation of alkaline phosphatase recombinantly produced in *Pichia pastoris* using endoglycosidase H. Nevertheless, even if deglycosylation is performed exhaustively, endoglycosidase H does not completely remove all glycan residues from the glycosylated protein but leaves one N-acetylglucosamine residue attached to the asparagines residue of the polypeptide chain. The residual N-acetylglucosamine residue may still serve as a target for the coupling reaction when forming a conjugate. The same applies to O-linked glycans, if present, which are not the preferred substrate of endoglycosidase H.

Figure 4:
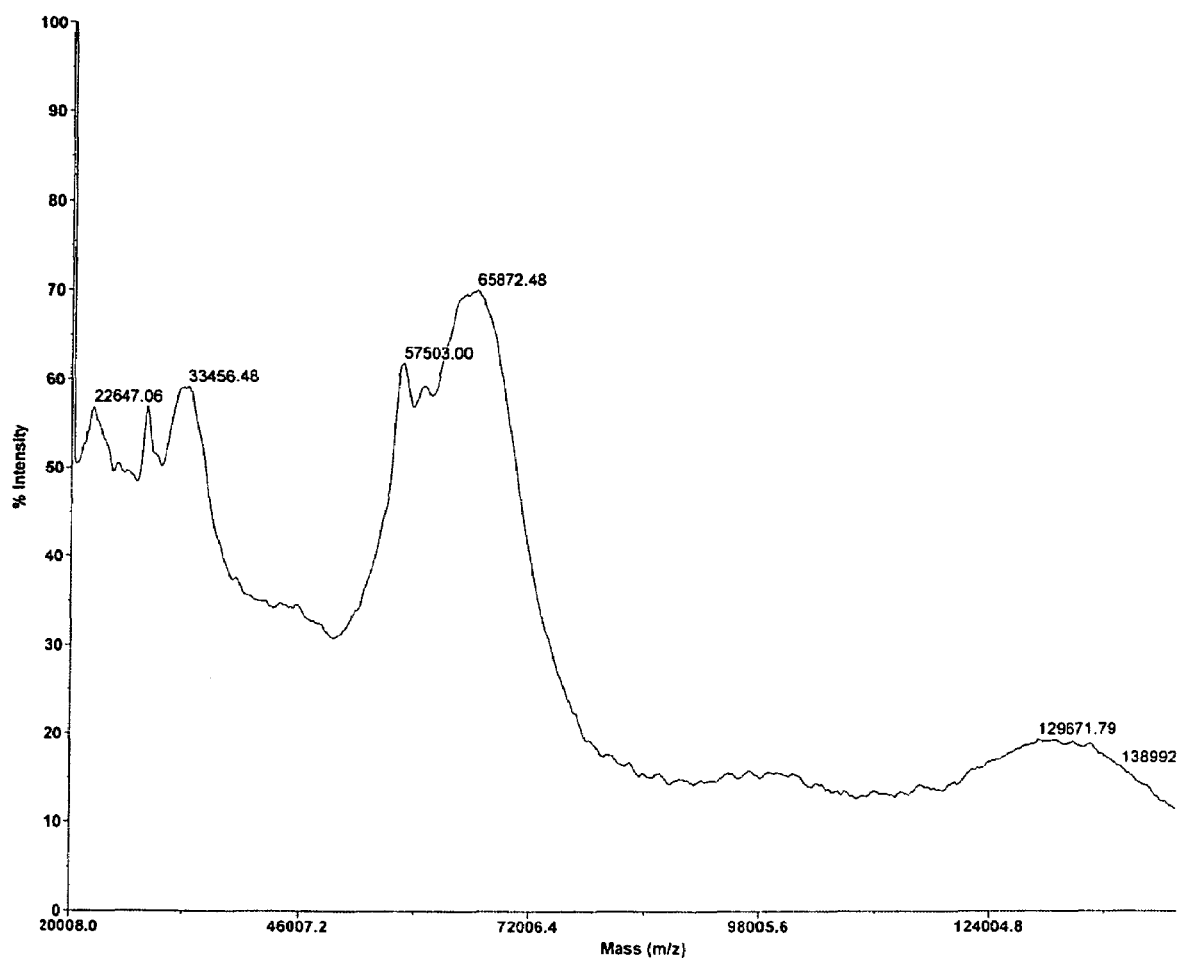
FIG. 4 is a graph showing determination of molecular weight of bovine alkaline phosphatase according to SEQ ID NO: 1 recombinantly produced in *Pichia pastoris*. Results of MALDI-TOF-MS (see Example 5).
Figure 5:
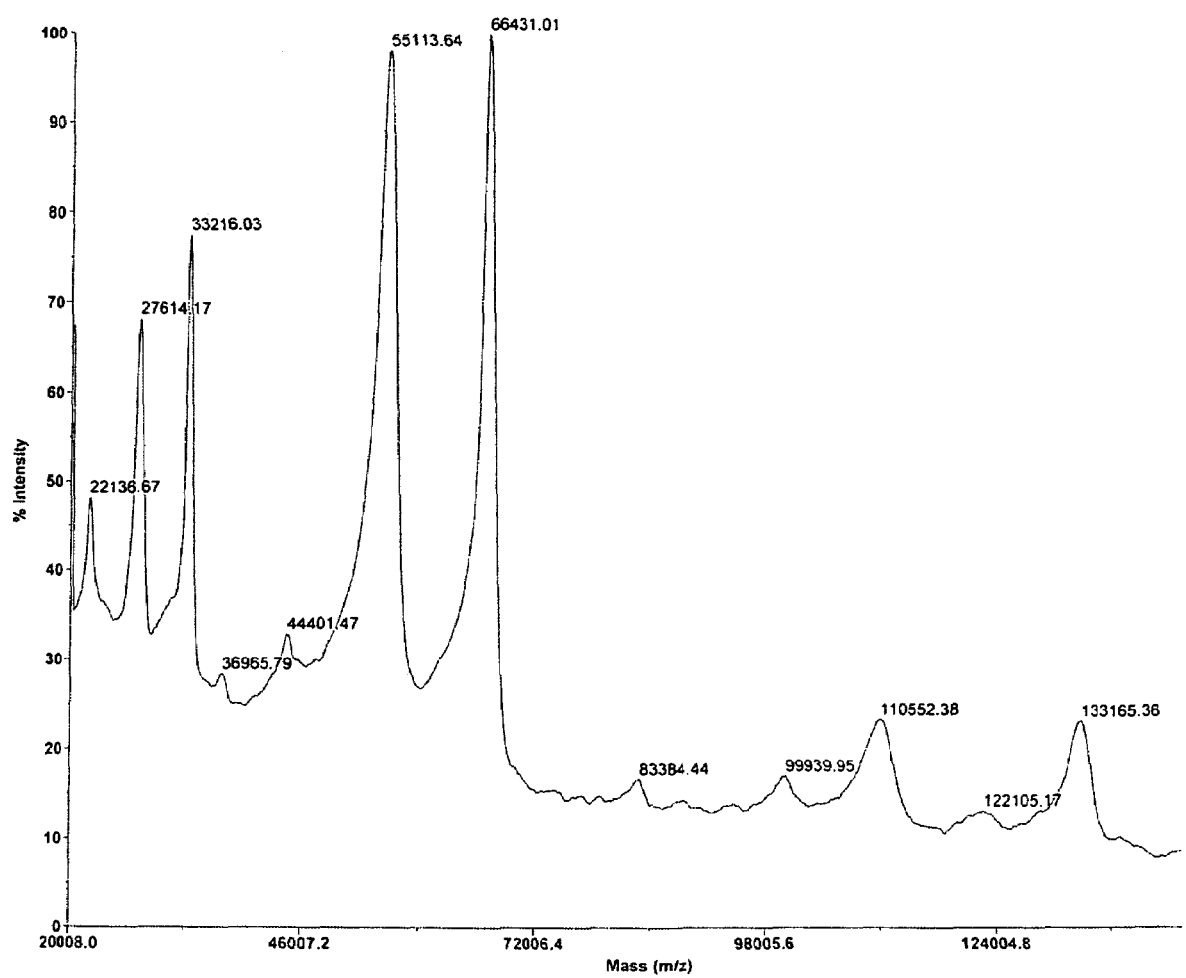
FIG. 5 is a graph showing determination of molecular weight of bovine alkaline phosphatase according to SEQ ID NO: 1 recombinantly produced in *Pichia pastoris* following endo H treatment. Results of MALDI-TOF-MS (see Example 5).

An enzyme that is produced recombinantly in yeast is usually inhomogeneous with regard to molecular weight. This is exemplified by bovine alkaline phosphatase having the amino acid sequence of SEQ ID NO: 1 recombinantly produced in *Pichia pastoris*. FIG. 4 shows a first result of MALDI-TOF-MS analysis, whereby the peak maxima indicating molecular weights of 57,503.0 and 65,872.48 correspond to glycosylated alkaline phosphatase monomers with differing degrees of glycosylation. FIG. 5 shows a second result of MALDI-TOF-MS analysis, whereby the peak maximum indicating the molecular weight of 55,113.64 corresponds to deglycosylated alkaline phosphatase monomers. The neighbouring peak at 66,431.01 corresponds to an internal standard. The second result was obtained under conditions permitting exhaustive or almost exhaustive digestion using endoglycosidase H. Thus, under these conditions up to about 80% of glycan residues are cleaved off.

Thus, another preferred embodiment of the invention is a method to produce a conjugate of a molecule capable of binding to a target molecule and an enzyme, comprising the steps of (a) providing a glycosylated enzyme, (b) partially deglycosylating the enzyme of step (a), (c) isolating the partially deglycosylated enzyme, (d) attaching the partially deglycosylated enzyme of step (c) to the molecule capable of binding to a target molecule.

It is preferred that the enzyme of step (a) is obtained by expression in a transformed yeast and isolated therefrom. It is more preferred that the carbohydrate portion of the glycosylated enzyme contains multiple mannose subunits.

It is also preferred that in step (b) between 10% and 99% of the carbohydrate residues are cleaved off from the glycosylated enzyme. It is more preferred that between 20% and 70% of the carbohydrate residues are cleaved off from the glycosylated enzyme. It is even more preferred that about 60% of the carbohydrate residues are cleaved off from the glycosylated enzyme, whereby "about" denotes an interval between 50% and 70%. Partial deglycosylation offers the possibility to use chemical reactions targeting residual carbohydrate residues of the enzyme when forming a conjugate of the enzyme and a molecule capable of binding to a target molecule.

Purifying from native mammalian host tissue an enzyme to be used for forming a conjugate bears the risk that an unwanted compound such as an inhibitor or a pathogen may copurify. E.g., alkaline phosphatase isolated from bovine tissue may be contaminated with pathogenic bovine prion protein. For this reason, recombinant expression of the desired enzyme in a microbial host such as yeast is preferred. Very much preferred is a methylotrophic yeast as a microbial host. The desired enzyme recombinantly expressed in and/or secreted by a transformed yeast as the microbial host is free of mammalian protein, and particularly free of mammalian pathogens.

Therefore yet another embodiment of the invention is a method to produce a conjugate of a molecule capable of binding to a target molecule and an enzyme, comprising the steps of (a) providing a glycosylated enzyme free of mammalian protein, (b) deglycosylating the enzyme of step (a), (c) isolating the deglycosylated enzyme, (d) attaching the deglycosylated enzyme of step (c) to the molecule capable of binding to a target molecule. It is preferred that step (b) consists of partially deglycosylating the enzyme of step (a). It is more preferred that in step (b) between 10% and 99% of the carbohydrate residues are cleaved off from the glycosylated enzyme. It is even more preferred that between 20% and 70% of the carbohydrate residues are cleaved off from the glycosylated enzyme. It is even more preferred that about 60% of the carbohydrate residues are cleaved off from the glycosylated enzyme.

In another preferred embodiment of the invention, the enzyme is an alkaline phosphatase, whereby the amino acid sequence of the alkaline phosphatase comprises a glycosylation site that is recognized in the transformed host organism expressing the alkaline phosphatase.

The term "alkaline phosphatase" denotes a member of the family of alkaline phosphatases. Alkaline phosphatases are dimeric, zinc-containing, non-specific phosphomonoesterases which occur in prokaryotic as well as in eukaryotic organisms, e.g. in *E. coli* and mammals (McComb et al., Alkaline Phosphatases Plenum Press, New York, 1979). Comparison of the primary structures of various members of the family of alkaline phosphatases show a high degree of homology (25-30% homology between *E. coli* and mammalian alkaline phosphatases; Millan, J. L., Anticancer Res. 8 (1988) 995-1004; Harris, H., Clin. Chim. Acta 186 (1990) 133-150). In humans and higher animals the family of alkaline phosphatases comprises four members that are located in different gene loci (Millan, J. L., Anticancer Res. 8 (1988) 995-1004; Harris, H., Clin. Chim. Acta 186 (1990) 133-150). The alkaline phosphatase family in humans and higher animals includes the tissue-specific alkaline phosphatases (placental alkaline phosphatase, germ cell alkaline phosphatase and intestinal alkaline phosphatase) and the non-tissue specific alkaline phosphatases which are primarily located in the liver, kidney and bones.

In yet another preferred embodiment of the invention, the alkaline phosphatase is of eukaryotic origin. In yet another preferred embodiment of the invention, the alkaline phosphatase is of human or bovine origin.

The term "alkaline phosphatase" further includes variants of alkaline phosphatases. A variant of an alkaline phosphatase, that is to say a variant of a wildtype alkaline phosphatase, denotes a protein that is an allelic form of a wildtype alkaline phosphatase, generated by way of amino acid exchange, amino acid insertion, amino acid deletion, or terminal addition of one or more amino acids. In a preferred variant of an alkaline phosphatase up to 10% of the amino acids in the amino acid sequence of the variant of the alkaline phosphatase are different compared to the amino acid sequence of the wildtype alkaline phosphatase from which the variant is derived.

Even more preferred is a variant of an alkaline phosphatase, whereby the variant is capable of being glycosylated, that is to say the variant includes a glycosylation site.

There are also genetic engineering methods of fusion protein expression in eukaryotic host organisms, characterized in that there is an additional sequence of amino acids fused to the amino acid sequence of a desired protein. Examples of an additional sequence of amino acids are biotinylation peptides (e.g. WO 95/04069) and Histidine-tags (Janknecht, R., et al., Proc. Natl. Acad. Sci. USA 88 (1991) 8972-8976).

It is also known to the art that certain amino acids at specific positions in the alkaline phosphatase amino acid sequence have a specific influence on the activity of an enzyme. EP 0 955 369 describes a highly active alkaline phosphatase.

Another embodiment of the invention is a method to produce a conjugate of a molecule capable of binding to a target molecule and an alkaline phosphatase, comprising the steps of (a) expressing an alkaline phosphatase in a methylotrophic yeast, whereby the polypeptide of the alkaline phosphatase includes a glycosylation site, and isolating the glycosylated alkaline phosphatase, (b) partially deglycosylating the alkaline phosphatase of step (a), (c) isolating the partially deglycosylated alkaline phosphatase, (d) attaching the partially deglycosylated alkaline phosphatase of step (c) to the molecule capable of binding to a target molecule. It is preferred that the alkaline phosphatase is of mammalian origin and even more preferred of bovine origin. Therefore, in a very much preferred embodiment of the invention, the alkaline phosphatase is an alkaline phosphatase comprising the amino acid sequence of SEQ ID NO: 1. In yet another very much preferred embodiment of the invention, the alkaline phosphatase is an alkaline phosphatase consisting of a dimer of two proteins whereby the polypeptide chain of each protein comprises the amino acid sequence of SEQ ID NO: 1. In yet another very much preferred embodiment of the invention, the alkaline phosphatase is an alkaline phosphatase consisting of a dimer of two proteins whereby the polypeptide chain of each protein consists of the amino acid sequence of SEQ ID NO: 1.

In yet another preferred embodiment of the invention, the molecule capable of binding to a target molecule is selected from the group consisting of (a) an antibody, or a functional fragment thereof, (b) avidin, or a polymer of avidin molecules, or a fragment of avidin capable of binding biotin, or a polymer of avidin fragments capable of binding biotin, (c) streptavidin, or a polymer of streptavidin molecules, or a fragment of streptavidin capable of binding biotin, or a polymer of streptavidin fragments capable of binding biotin, (d) a lectin, or a fragment thereof capable of binding carbohydrate, (e) a hapten, (f) a nucleic acid or an analog thereof.

In yet another preferred embodiment of the invention, the molecule capable of binding to a target molecule is attached to the enzyme by means of a linking group.

A further aspect of the invention is an isolated and partially deglycosylated enzyme of mammalian origin, whereby the enzyme is free of mammalian proteins, obtainable by a method comprising the steps of (a) providing a glycosylated enzyme obtained by expression in a transformed yeast and isolated therefrom, whereby the carbohydrate portion of the glycosylated enzyme contains multiple mannose subunits, (b) partially deglycosylating the enzyme of step (a), (c) isolating the partially deglycosylated enzyme. It is preferred that the enzyme is an alkaline phosphatase. It is more preferred that the enzyme is a human or a bovine alkaline phosphatase. It is even more preferred that the alkaline phosphatase comprises the amino acid sequence of SEQ ID NO: 1. It is even more preferred that the alkaline phosphatase contains a subunit comprising the amino acid sequence of SEQ ID NO: 1. It is even more preferred that a subunit of the the alkaline phosphatase consists of the amino acid sequence of SEQ ID NO: 1. The protein according to SEQ ID NO: 1 forms a dimer, i.e. two monomeric subunits associate. It is preferred that the molecular weight of a subunit of the alkaline phosphatase is between 54 kDa and 58 kDa. It is even more preferred that the molecular weight of the alkaline phosphatase is about 55 kDa, that is to say between 54.5 kDa and 56 kDa.

A further aspect of the invention is the use of an enzyme, obtainable by a method according to the invention, for forming a conjugate. Preferred is the use of a partially deglycosylated enzyme, obtainable by a method according to the invention, for forming a conjugate.

A further aspect of the invention is a conjugate of a molecule capable of binding to a target molecule and an enzyme, obtainable by a method according to the invention. Preferred is a conjugate of a molecule capable of binding to a target molecule and partially deglycosylated enzyme obtainable by a method according to the invention.

A further aspect of the invention is the use of a conjugate according to the invention in an assay for detecting the presence or determining the quantity of a target molecule. In a preferred embodiment of the invention, the assay is an enzyme immunoassay. In another preferred embodiment of the invention, the enzyme immunoassay is a heterogeneous or homogeneous enzyme immunoassay.

A further aspect of the invention is a kit of parts, comprising a molecule capable of binding to a target molecule attached to a solid phase, a conjugate according to the invention, an incubation buffer, and a substrate capable of being converted by the enzyme portion of the conjugate.

The following examples, references, sequence listing and figures are provided to aid the understanding of the present invention, the true scope of which is set forth in the appended claims. It is understood that modifications can be made in the procedures set forth without departing from the spirit of the invention.

In order that the invention may be more readily understood, reference is made to the following examples, which are intended to illustrate the invention, but not limit the scope thereof.

SPECIFIC EMBODIMENTS

Example 1

Deglycosylation of Recombinantly Produced Alkaline Phosphatase 10 mg recombinantly produced alkaline phosphatase (also referred to in the figures as "recAP") isolated from *Pichia pastoris* were incubated with 200 milliunits of endoglycosidase H ("endo H", Roche cat. No. 1643053) in 1 ml of sodium acetate buffer 30 mM, pH 5.5, containing 1 mM $MgCl_2$ and 1.5 M NaCl for 2 h. After this time the solution was exhaustively dialysed in a filtration chamber with a YM 30 membrane using a triethanolamin/HCl buffer, pH 7.6, containing 150 mM NaCl, 1 mM $MgCl_2$ and 0.1 mM $ZnCl_2$, resulting in an end volume of 1 ml. FIG. 1 illustrates the elution times on a TSK 3000 column of the recombinantly produced alkaline phosphatase before and after the endo H treatment. It can be seen that the peak eluting at 6.88 min before treatment has completely disappeared and a new peak eluting at 7.61 min has shown up, indicating that the recombinantly produced alkaline phosphatase has lost glycan chains resulting in a smaller molecular weight and a later elution time compared to the unchanged molecule.

Example 2

Measurement of AP Enzyme Activity

Enzyme activity of alkaline phosphatase was determined using 4-nitrophenyl-phosphate as substrate according to the test protocol described (Z. Klin. Chem. Klin. Biochem. 8 (1970) 658-660; and Z. Klin. Chem. Klin. Biochem. 10 (1972) 182). Recombinantly produced alkaline phosphatase from *Pichia pastoris* revealed a specific activity of about 7,000 U/mg which was not altered by the endoglycosidase H treatment.

Example 3

Preparation of Alkaline Phosphatase Conjugates

Activation of AP 5 mg of the respective alkaline phosphatase preparation (recombinantly produced alkaline phosphatase; recombinantly produced alkaline phosphatase/endo H-treated) dissolved in 0.5 ml sodium phosphate buffer 30 mM, pH 7.1, were mixed with 0.059 mg of N-succinimidyl-S-acetylthiopropionat (SATP) dissolved in 12 µl DMSO and stirred for 1 h at room temperature (RT). The reaction was stopped by the addition of 5 µl 1 M lysine-HCl and stirred for another 30 min at room temperature (RT). The reaction mixture was then exhaustively dialysed overnight at 4° C. against 1.5 l of 10 mM potassium phosphate buffer, pH 6.1, containing 50 mM NaCl.

Activation of Anti-Human Chorionic Gonadotropin (hCG) Immunoglobulin 20 mg of monoclonal antibody anti-hCG-M-INN22-IgG dissolved in 1 ml of 30 mM sodium phosphate buffer pH 7.1 were mixed with 0.205 mg maleimidohexanoyl-N-hydroxysuccinimid ester (MHS) dissolved in 21 µl DMSO and stirred for 1 h at RT. The reaction was stopped by the addition of 5 µl 1 M lysine-HCl and stirred for another 30 min at RT. The reaction mixture was then exhaustively dialysed overnight at 4° C. against 5 l of 10 mM potassium phosphate buffer, pH 6.1, containing 50 mM NaCl.

Preparation of the Conjugates

Three (3) mg of the respective SATP-activated AP preparations (recombinantly produced alkaline phosphatase; recombinantly produced alkaline phosphatase/endo H-treated) dissolved in 324 µl of 10 mM potassium phosphate buffer, pH 7.5, containing 50 mM NaCl, were mixed with 8 µl of 1 M hydroxylamine solution and stirred for 1 h at RT. After that time 1.74 mg of MHS-activated anti-hCG-M-INN22-IgG dissolved in 262 µl of 10 mM potassium phosphate buffer, pH 7.5, containing 50 mM NaCl, were added and the reaction mixture stirred for 2 h at RT. Then 7 µl of 0.2 M cystein-HCl solution (adjusted to pH 6.7 by addition of 1 M phosphoric acid) were added and stirred for 30 min at RT. After that 7 µl of 0.5 M N-methylmaleimid solution in water were added and stirred for another 30 min at RT. The reaction mixture was then exhaustively dialysed overnight at 4° C. against 1.5 l of 50 mM triethanolamine-HCl buffer, pH 7.6, containing 150 mM NaCl, 1 mM $MgCl_2$ and 0.1 mM $ZnCl_2$. After dialysis the solution was brought to a NaCl concentration of 3 M and stored at +4° C. until use.

Figure 2:
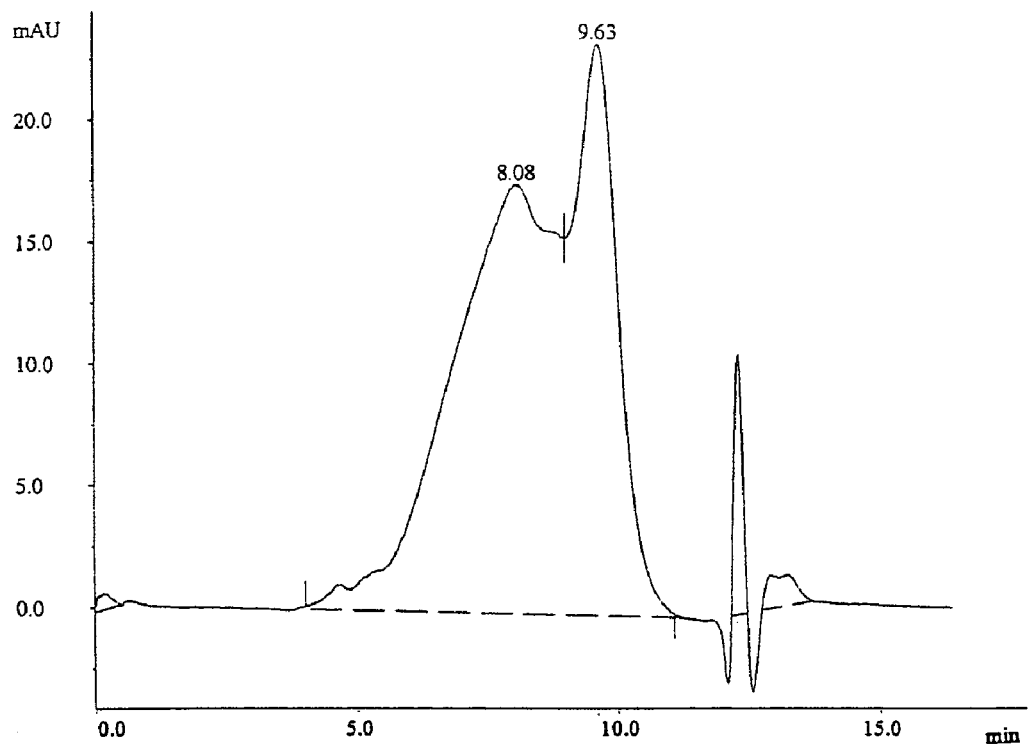
FIG. 2 is a graph showing profiles of recombinantly produced alkaline phosphatase/anti-human chorionic gonadotropin (hCG)-IgG (part A) and recombinantly produced alkaline phosphatase (endo H treated)/anti-hCG-IgG (part B) conjugates after 2 hours of reaction time, separated on a TSK 4000 chromatography column. The solid line demonstrates the protein absorption at 280 nm.
Figure 2:
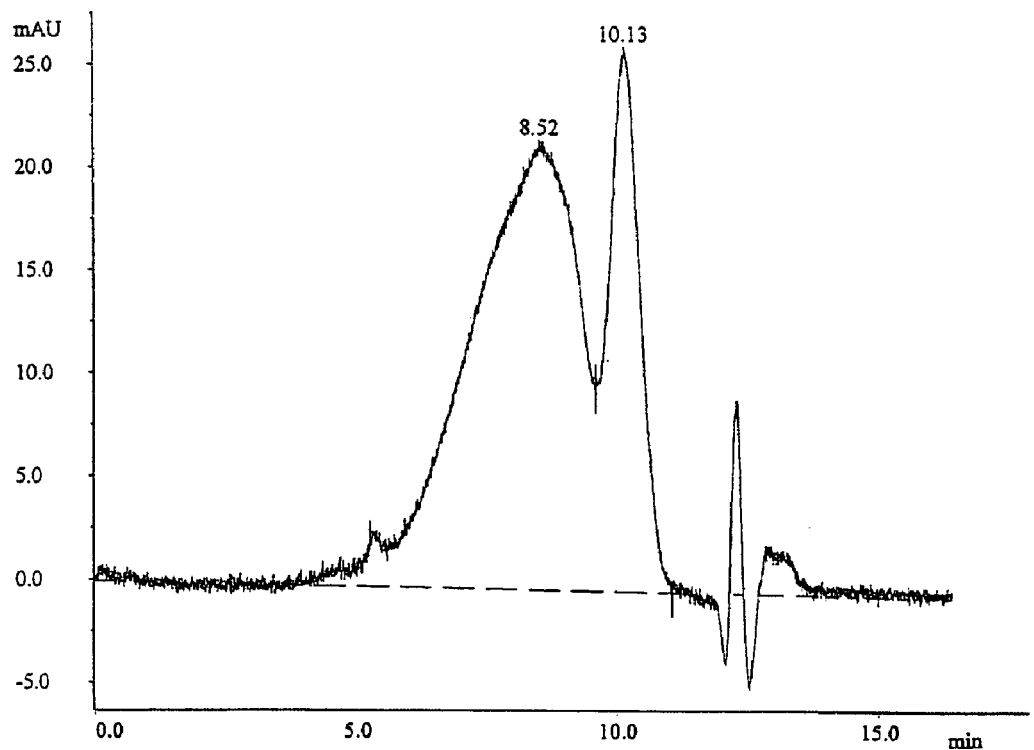

FIG. 2 displays the results of the conjugations after 2 h for recombinantly produced alkaline phosphatase/anti-hCG-IgG (part A) and recombinantly produced alkaline phosphatase (endo H-treated)/anti-hCG-IgG (part B) in form of a separation of the reaction mixtures on a TSK 4000 column. It can be seen that the conjugate peak in part A (maximum at 8.08 min elution time) is not as well separated from the not conjugated recombinantly produced alkaline phosphatase peak (elution at 9.63 min) as it is the case in part B, were the bulk of the conjugate (elution maximum at 8.52 min) is much better separated from the not derivatized recombinantly produced alkaline phosphatase/endo H-treated (elution maximum at 10.13 min), resulting in a much better yield of this conjugate compared to that in part A. The conjugates were pooled as indicated in the figure and used for further analysis.

Example 4

Comparison of the Conjugates by hCG ELISA

The hCG ELISA was performed as a sandwich assay by using streptavidin-coated microtiterplates. Biotinylated Mab anti-hCG-M-1F79-Fab derivative was used as the immobilized binding partner (150 µl of a 5 µg/ml solution in incubation buffer per well were incubated for 30 min at RT). After 3 times washing 120 µl of hCG samples in concentrations of 0, 14.84, 254.8, 2103 and 7801 mU/ml, respectively, dissolved in incubation buffer, were added per well and incubated for 1 h at RT. After 3 times washing 100 µl of the respective alkaline phosphatase/Mab anti-hCG-M-INN22-IgG conjugates described above were added and incubated for 1 h at RT. After 3 times washing 100 µl per well of a 100 mM 4-nitrophenylphosphate substrate solution were added and after 20 min incubation at RT the absorption was measured with an ELISA reader at 405 nm using 490 nm as a correction wavelength.

Incubation buffer: Potassium phosphate 50 mM, sodium chloride 150 mM, 1% bovine serum albumin, 0.05% TWEEN 20 (ICI Americas Inc), pH 7.5.

Figure 3:
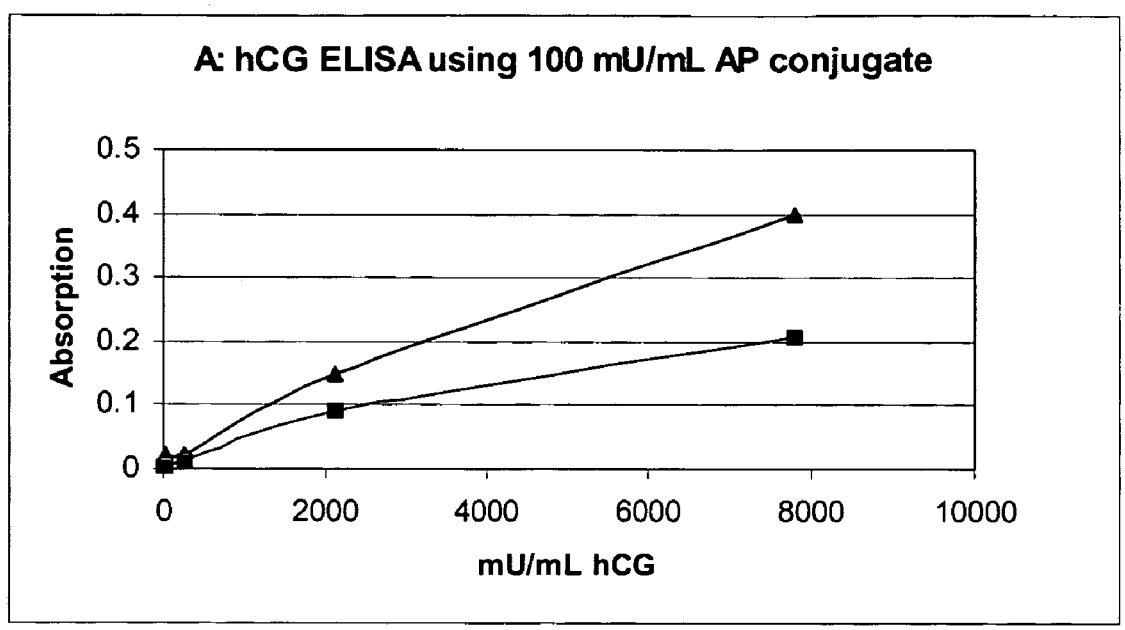
FIG. 3 is a graph showing measurements of hCG in an MTP (microtiter plate) ELISA using recombinantly produced alkaline phosphatase/anti-hCG-IgG conjugate (squares) and recombinantly produced alkaline phosphatase (endo H treated)/anti-hCG-IgG (triangles). In part A 100 mU/ml, and in part B 42 ng/ml of either conjugate were employed.
Figure 3:
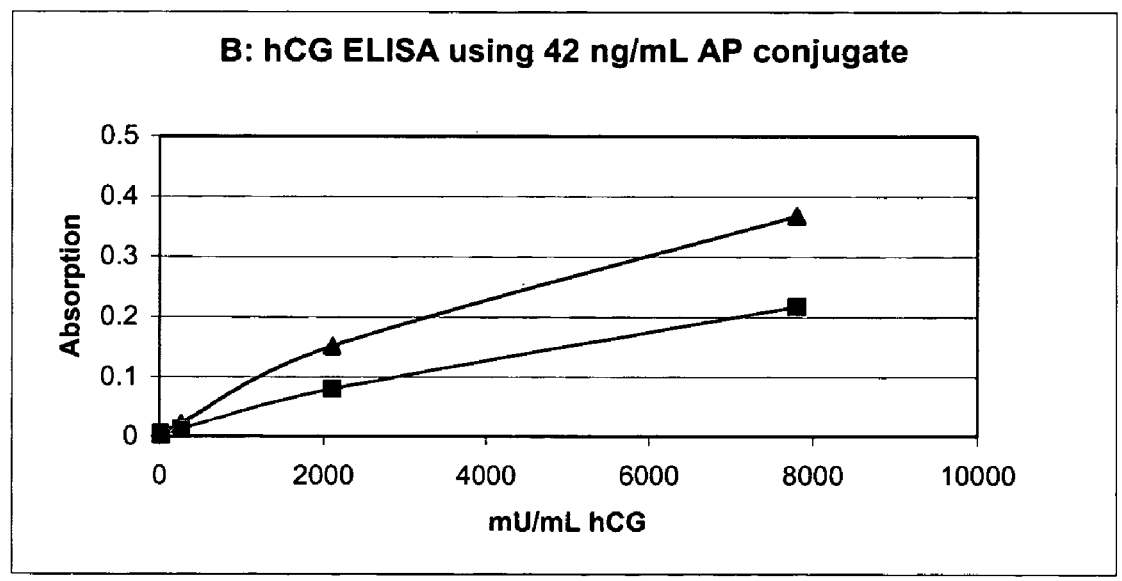

For comparison of the conjugates two analytical series were performed. In the first series the conjugates were added at a concentration of 100 mU/ml each, and in the second 42 ng/ml of the respective conjugates were used, and FIG. 3 illustrates the results obtained. It can be seen that the conjugate with recombinantly produced alkaline phosphatase (endo H-treated) as label performs better in either case compared to recombinantly produced alkaline phosphatase from *Pichia pastoris* with the N-glycan chains still present (part A using 100 mU/ml of each conjugate; part B using 42 ng/ml).

Example 5

Determination of the Molecular Weight of Endo H Deglycosylated recAP by MALDI-TOF MS (Matrix-assisted Laser Desorption Ionization Time-of-Flight Mass Spectrometry)

recAP produced in *Pichia pastoris* was treated by endo H as described in Example 1 and dialyzed against distilled water. The protein solution was mixed with sinapic acid matrix solution and was crystallized on the target. The samples were analyzed on a Voyager Biospectrometry workstation equipped with delayed extraction, in the positive mode.

The peak maxima corresponding to a molecular weight of recAP before deglycosylation were determined at 57,503 and 65,872.48 Da and after deglycosylation at 55,113.64 Da (see FIGS. 4 and 5).

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method to produce a conjugate of an alkaline phosphatase enzyme and an antibody or functional fragment thereof which binds to a target molecule in a detection assay, wherein the alkaline phosphatase enzyme comprises at least one glycosylation site that is recognized in a transformed yeast expression host, the method comprising the steps of:
   (a) providing a glycosylated alkaline phosphatase enzyme comprising the amino acid sequence set forth as SEQ ID NO: 1 and obtained by expression in the transformed yeast and isolated therefrom,
   (b) at least partially deglycosylating the glycosylated enzyme of step (a),
   (c) isolating the deglycosylated enzyme, and
   (d) attaching the deglycosylated enzyme of step (c) to the antibody or functional fragment thereof capable of binding to a target molecule in a detection assay.

2. The method according to claim 1, wherein step (b) comprises cleavage of between 10% and 99% of carbohydrate residues from the glycosylated enzyme.

3. The method according to claim 1, wherein in step (b) comprises cleavage of between 20% and 70% of carbohydrate residues from the glycosylated enzyme.

4. The method according to claim 1, wherein in step (b) comprises cleavage of about 60% of carbohydrate residues from the glycosylated enzyme.

5. The method according to claim 1, wherein the glycosylated enzyme of step (a) is free of mammalian protein.

6. The method according to claim 1, wherein the glycosylated enzyme of step (a) is free of mammalian pathogens.

7. The method according to claim 1 wherein the alkaline phosphatase is of eukaryotic origin.

8. The method according to claim 1, wherein in step (b) the enzyme is deglycosylated or partially deglycosylated by a chemical reagent or an enzyme selected from the group consisting of an amidase, an exoglycosidase, and an endoglycosidase.

9. The method according to claim 8, wherein in step (b) the enzyme is deglycosylated or partially deglycosylated by endo-β-N-acetylglucosaminidase H, endo-β-N-acetylglucosaminidase F, or peptide-N-glycosidase F, or a combination thereof.

10. The method according to claim 1, wherein the molecule which binds to a target molecule is attached to the deglycosylated enzyme by means of a linking group.

11. A conjugate of an enzyme and a molecule which binds to a target molecule, obtainable by the method according to claim 5 wherein the glycosylated enzyme of step (a) is free of mammalian pathogens.

12. A kit of parts, comprising a molecule which binds to a target molecule attached to a solid phase, a conjugate according to claim 11, an incubation buffer, and a substrate which is converted by the enzyme portion of the conjugate.

* * * * *